(12) United States Patent
Hernandez et al.

(10) Patent No.: US 8,884,006 B2
(45) Date of Patent: Nov. 11, 2014

(54) SMALL-MOLECULE INHIBITORS OF RAC1 IN METASTATIC BREAST CANCER

(71) Applicant: University of Puerto Rico, San Juan, PR (US)

(72) Inventors: Eliud Hernandez, San Juan, PR (US); Cornelis Vlaar, San Juan, PR (US); Suranganie Dharmawardhane, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 13/622,303

(22) Filed: Sep. 18, 2012

(65) Prior Publication Data

US 2013/0172552 A1    Jul. 4, 2013

Related U.S. Application Data

(60) Provisional application No. 61/536,065, filed on Sep. 19, 2011.

(51) Int. Cl.
*C07D 413/00* (2006.01)
*C07D 413/14* (2006.01)
*C07D 403/12* (2006.01)

(52) U.S. Cl.
CPC ............ *C07D 413/14* (2013.01); *C07D 403/12* (2013.01)
USPC ....................................................... 544/122

(58) Field of Classification Search
USPC ....................................................... 544/122
See application file for complete search history.

(56) References Cited

FOREIGN PATENT DOCUMENTS

WO    WO 0012485 A1 *  3/2000

OTHER PUBLICATIONS

Brenda L. Montalvo-Ortiz et al., 287 The Journal of Biological Chemistry, 132228-13238 (2012).*

* cited by examiner

*Primary Examiner* — James O. Wilson
*Assistant Examiner* — Alexander R Pagano
(74) *Attorney, Agent, or Firm* — Hoglund & Pamias, PSC; Roberto J. Rios

(57) ABSTRACT

A novel inhibitor of Rac activity based on the structure of the established Rac/Rac-GEF inhibitor NSC23766 is discloses. The compound EHop-016, with an IC50 of 1.1 μM, is a 100-fold more efficient inhibitor of Rac activity than NSC23766. EHop-016 is specific for Rac1 and Rac3 at concentrations ≤5 mM. At higher concentrations, EHop-016 inhibits the close homolog Cdc42. In MDA-MB-435 cells, EHop-016 (≤5 mM) inhibits the association of the Rac-GEF Vav2 with a nucleotide-free Rac1(G15A), which has a high affinity for activated GEFs. EHop-016 does not affect the association of the Rac-GEF Tiam-1 with Rac1(G15A) at similar concentrations. EHop-016 also inhibits the Rac activity of MDA-MB-231 metastatic breast cancer cells and reduces Rac-directed lamellipodia formation in both cell lines. EHop-016 decreases Rac-downstream effects of p21-activated kinase (PAK)1 activity and directed migration of metastatic cancer cells. At low concentrations (<5 μM), EHop-016 does not affect cell viability.

2 Claims, 10 Drawing Sheets

Figure 1A
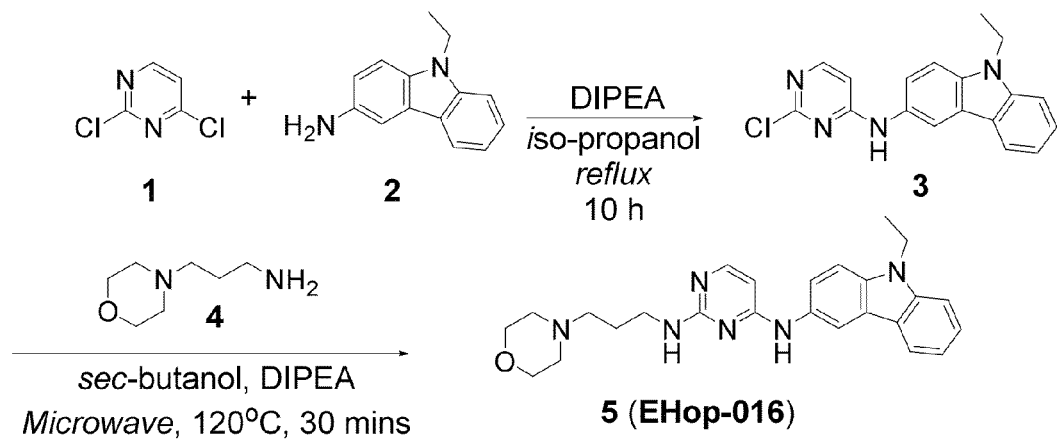
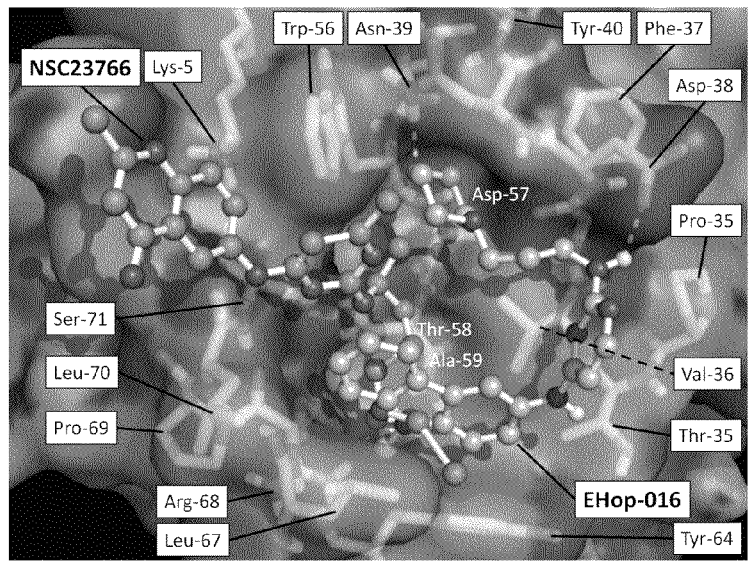
Figure 1B

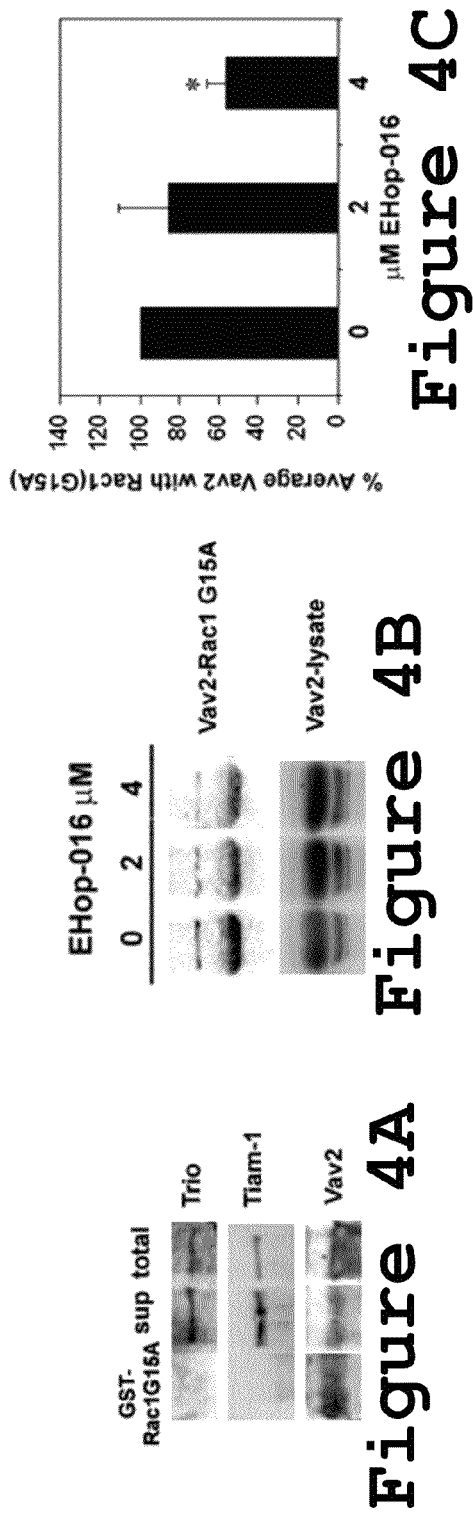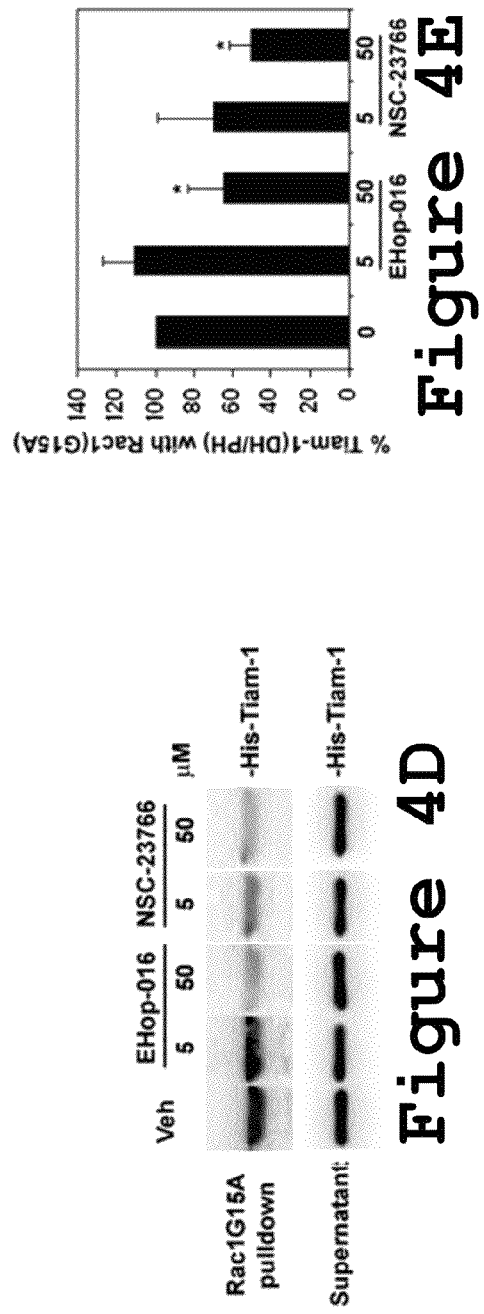

Figure 5A
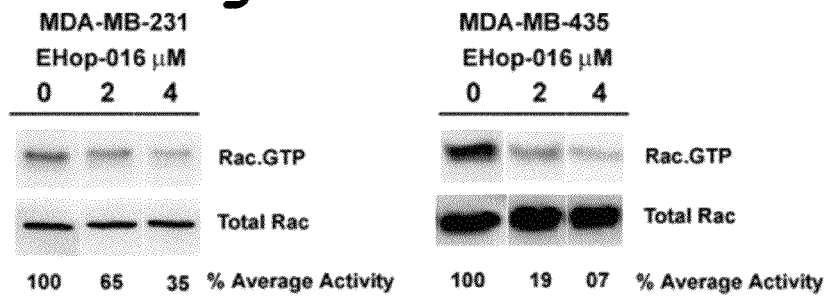
Figure 5B
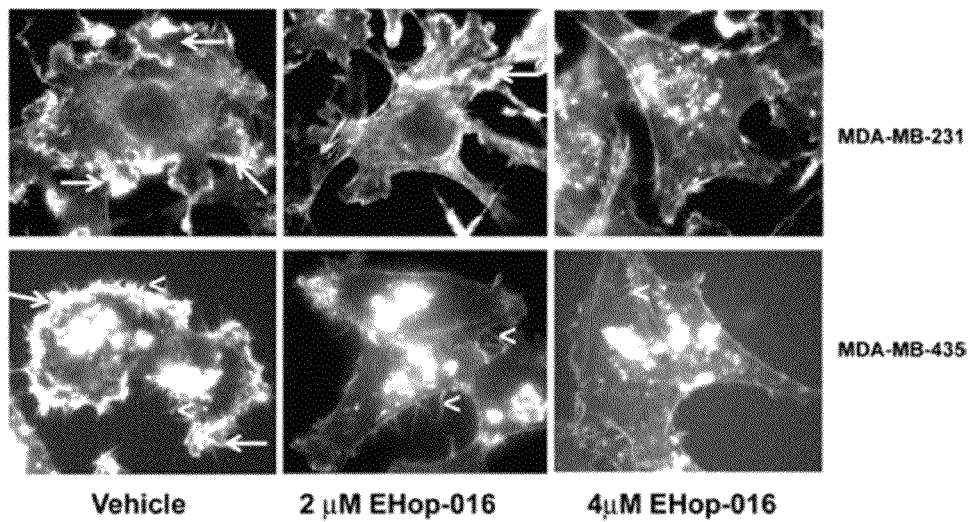
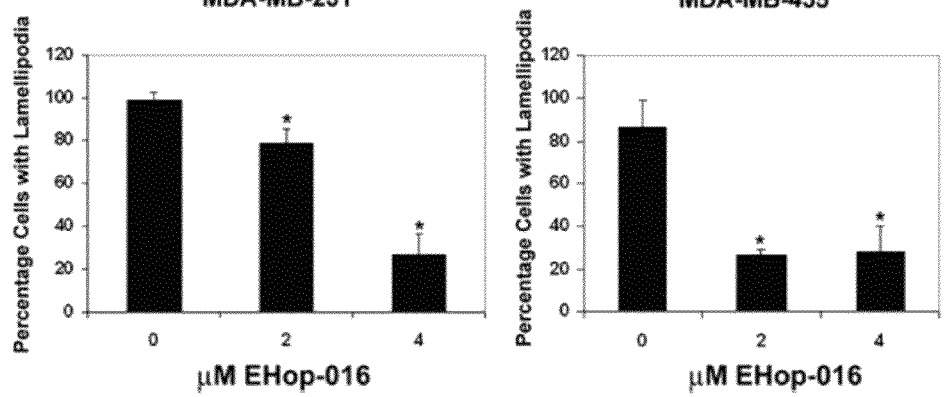

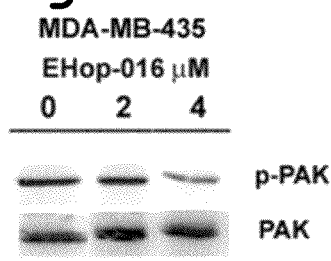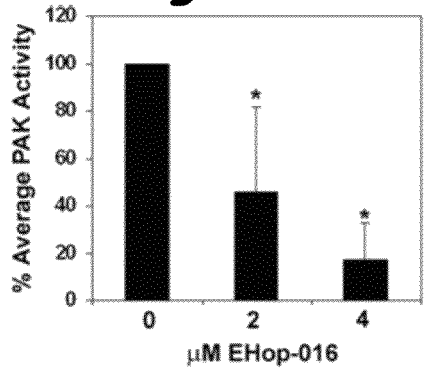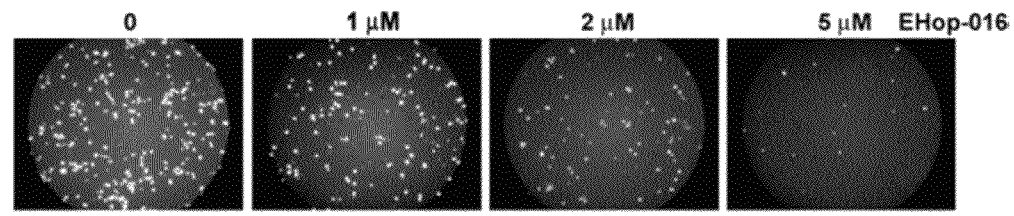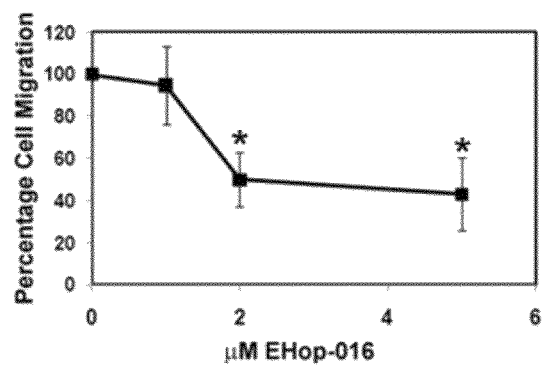
Figure 6A
Figure 6B
Figure 6C

Figure 8A
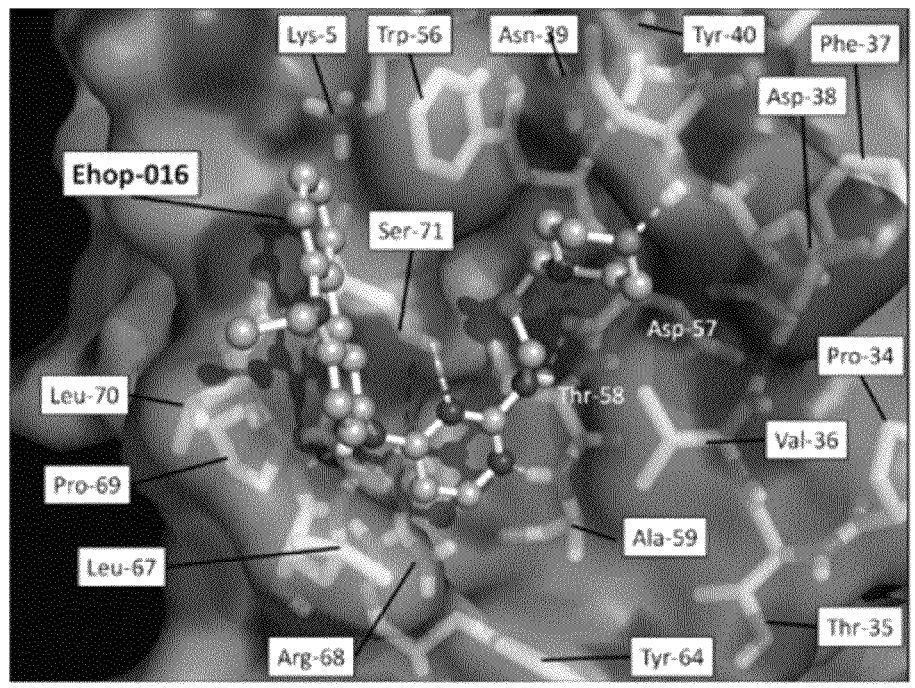
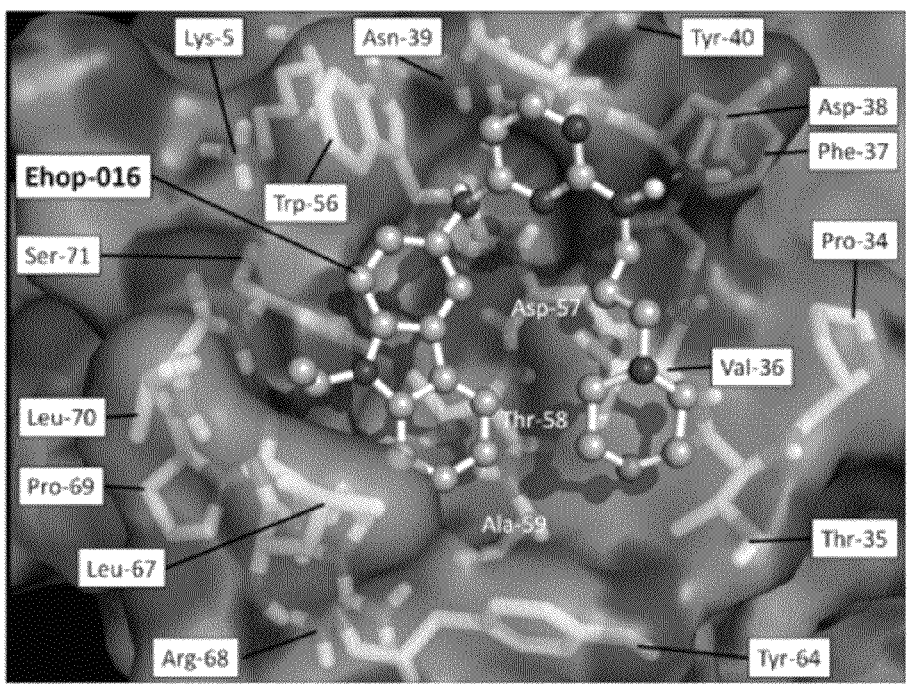
Figure 8B

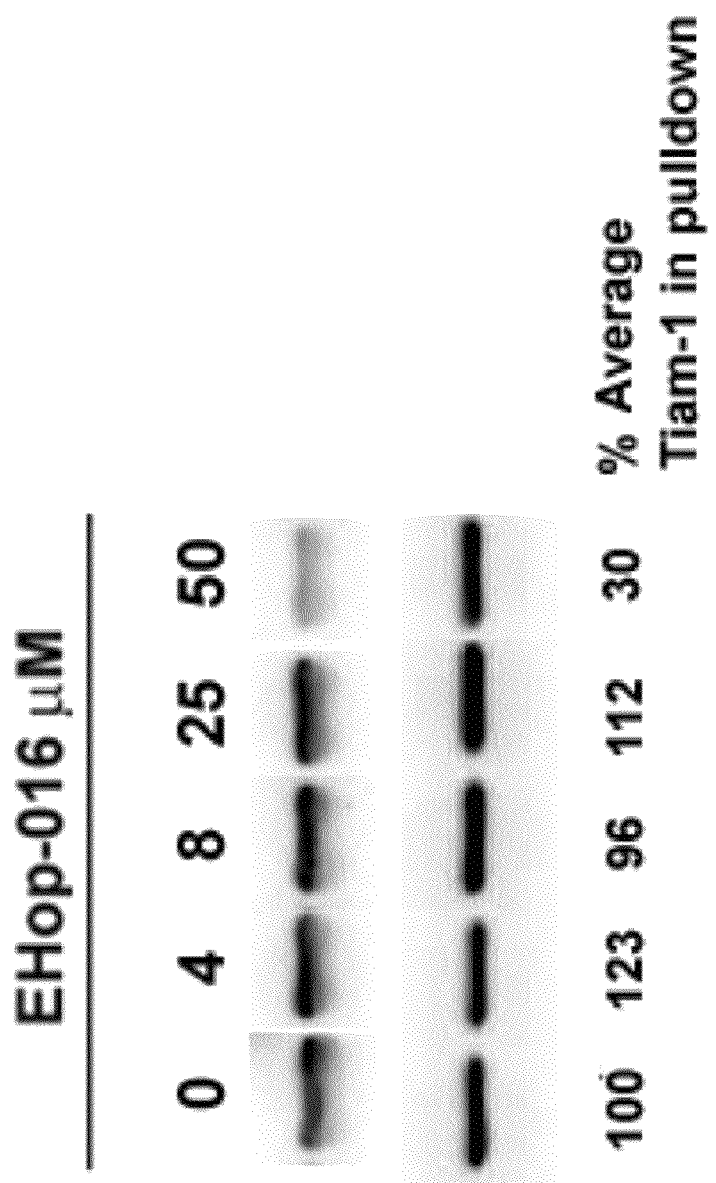

SMALL-MOLECULE INHIBITORS OF RAC1 IN METASTATIC BREAST CANCER

GOVERNMENT INTEREST

The claimed invention was made with U.S. Government support under grant number BCRP W81XWH-07-1-0330 awarded by the Department of Defense (DoD)/US Army and grant numbers SC3GM084824, G12RR035051, 5U54CA096297, and G12RR03035 from the National Institutes of Health (NIH). The government has certain rights in this invention.

BACKGROUND OF THE INVENTION

Rho family GTPases (Rho, Rac, Cdc42) are important intracellular signaling proteins that control diverse cellular functions, including actin cytoskeletal organization, invasion and metastasis, transcriptional regulation, cell cycle progression, apoptosis, vesicle trafficking, and cell-to-cell and cell-to-extracellular matrix adhesions. Consequently, Rho GTPases have been implicated in cancer, and the progression of other diseases by a large number of studies. Of the Rho family GTPases, Rac1 and Rac3, the isoforms expressed in non-hematopoietic cells, have been specifically implicated in rearrangement of the actin cytoskeleton into cell surface protrusions called lamellipodia or invadopodia that are specific for forward migration during invasion; and thus, have been implicated in promotion of metastasis. Racs have also been shown to be essential for Ras and other oncogene-mediated transformation. Our group and others as well, has implicated hyperactive Rac1 and Rac3 with increased survival, proliferation, and invasion of breast and brain cancers. Recent reports have shown a role for Rac in mammalian target of rapamycin (mTOR)-mediated regulation of cancer malignancy and anti breast cancer therapy resistance. Moreover, Rac1 was shown to increase Estrogen receptor-alpha (ERα)-mediated transcriptional activity in breast cancer. Studies have also demonstrated a cancer-promoting role for the constitutively active Rac1b splice variant that is overexpressed in breast and colorectal cancer. Since the malignant phenotype of Rac is associated with activation of its direct downstream effectors p21-activated kinases (PAKs), much effort has been focused on the development of PAK inhibitors as anti cancer therapeutics. However, in addition to PAK, Racs have multiple downstream effectors such as WAVE and Mena/VASP that contribute to cancer. Therefore, targeting Rac is a more viable approach for the development of anticancer drugs.

Unlike the related small GTPase Ras, Racs are not mutated in malignant cancers but rather overexpressed or hyperactivated. Racs are activated by GTP/GDP exchange catalyzed by guanine nucleotide exchange factors (GEF) that are regulated via a myriad of cell surface receptors. So far, over 60 potential Rac-GEFs have been identified. Of these, Dbl family GEFs such as T-cell invasion and metastasis gene product (Tiam-1) and Vav have been implicated in breast cancer progression. Tiam-1 expression has also been correlated with high breast cancer cell migration, indicating a specific role for Tiam-1 in breast cancer metastasis. Recent reports have also shown that $PIP_3$-dependent Rac exchanger 1 (p-Rex1) is upregulated in breast cancer cells and breast cancer patients with poor prognosis. Thus, elevation of Rac.GEF expression and/or activity appears to be a common phenomenon during cancer progression. Therefore, targeting the binding of Rac to GEFs is a rational strategy to inhibit Rac activity and thus, cancer invasion.

NSC23766 was identified as a small molecule that binds to a putative binding pocket in the surface groove of Rac1 that interacts with the Rac-specific GEFs Trio and Tiam1. NSC23766 has been shown to inhibit the anchorage-independent growth and invasion of human prostate cancer PC-3 cells, Rac activation and Rac-dependent aggregation of platelets stimulated by thrombin, Rac1 and Rac2 activities of hematopoietic stem/progenitor cells, and migration from mouse bone marrow to peripheral blood. NSC23766 has also been shown to inhibit invasion of chronic myelogenous leukemia cells in vitro and in vivo in a mouse model. Thus, such structure-function based rational design appears to represent a new avenue for generating small molecule inhibitors of Rac. However, NSC23766 is a moderately active Rac inhibitor with a relatively high $IC_{50}$ of 50-100 µM in fibroblasts, which limits its potential use as a therapeutic agent. In addition, our group has found that in the highly metastatic cancer cell line MDA-MB-435, NSC23766 inhibits Rac1 by only ~20% at a concentration of 50 µM, and that at this concentration there is no significant effect on lamellopodia formation. Therefore, there is a need for more effective inhibitors to reduce Rac activity in highly metastatic cancer cells.

The identification of novel inhibitors of Rac that function via different inhibitory mechanisms has been the subject of several studies. Thus, whereas NSC23766 inhibits the interaction of Rac1 with several of its GEFs, the Rac inhibitor EHT 1864 interferes with the interaction of Rac with its downstream effectors at concentrations of 10-50 µM. A virtual screening of a selected subset of compounds from the ZINC database for binding affinity to Rac1 based on the crystal structure of Rac1 with NSC23766, identified several novel Rac1 inhibitors with experimental $IC_{50}$ values ranging from 12.2-57 µM. In addition, a high-throughput flow-cytometry bead-based multiplex assay identified MLS000532223 as a compound that prevents GTP binding to Rac. However, other Rho GTPases, such as Cdc42, are also affected by this compound. Small molecule compounds have also been synthesized to specifically inhibit the Rac1b splice variant. Another report identified ITX3 as a GEF inhibitor that targeted Rac and RhoG interaction with Trio; however, this compound is effective at high 50-100 mM concentrations.

SUMMARY OF THE INVENTION

In an endeavor to develop novel more potent Rac inhibitors with possible clinical applications, the present invention uses NSC23766 as a lead structure for the design of compounds with 2-3 times enhanced potency. Thus, the present invention reports the identification and characterization of the biological activity of EHop-016, a novel NSC23766 derivative that inhibits Rac1 100-fold more effectively than the parent compound.

The compound EHop-016, with an IC50 of 1.1 µM, is a 100-fold more efficient inhibitor of Rac activity than NSC23766. EHop-016 is specific for Rac1 and Rac3 at concentrations ≤5 mM. At higher concentrations, EHop-016 inhibits the close homolog Cdc42. In MDA-MB-435 cells, EHop-016 (≤5 mM) inhibits the association of the Rac-GEF Vav2 with a nucleotide-free Rac1(G15A), which has a high affinity for activated GEFs. EHop-016 does not affect the association of the Rac-GEF Tiam-1 with Rac1(G15A) at similar concentrations. EHop-016 also inhibits the Rac activity of MDA-MB-231 metastatic breast cancer cells and reduces Rac-directed lamellipodia formation in both cell lines. EHop-016 decreases Rac-downstream effects of p21-activated kinase (PAK)1 activity and directed migration of metastatic cancer cells. At low concentrations (<5 μM), EHop-016 does not affect cell viability.

BRIEF DESCRIPTION OF THE DRAWINGS

Further features and advantages of the invention will become apparent from the following detailed description taken in conjunction with the accompanying figures showing illustrative embodiments of the invention, in which:

FIG. 1A shows a synthetic scheme for the preparation of EHop-016 according to the present invention.

FIG. 1B shows EHop-016 docked into GEF binding pocket of Rac1, and its comparison with the position of NSC23766 in the crystal structure of the Rac1-NSC23766 complex according to the present invention.

FIG. 4A shows a representative Western blot of GST-Rac1 (G15A) pull-down, supernatant (sup) from the incubation, and cell lysates, immunostained for Trio, Tiam-1, or Vav2 according to the present invention.

FIG. 4B shows a representative Western blot of GST-Rac1 (G15A) beads preincubated with vehicle (0), or 2 or 4_M EHop-016 prior to incubation with MDA-MB-435 cell lysates according to the present invention.

FIG. 4C shows quantification of the percentage of average Vav2 (two bands at ~100 kDa) associated with the Rac1 (G15A) beads from pull-down assays in the presence or absence of EHop-016 according to the present invention.

FIG. 4D shows a representative Western blot of GST Rac1 (G15A) pull-downs (Top), supernatants (Bottom) according to the present invention.

FIG. 4E shows quantification of percentage of Tiam-1 (DH/PH) domain associated with Rac1(G15A) beads in the presence or absence of EHop-016 or NSC23766 according to the present invention.

FIG. 5A shows representative Western blots (MDA-MB-231; MDA-MB-435) of pull-downs immunostained for Rac-GTP (top row) or total Rac in cell lysate (bottom row) according to the present invention.

FIG. 5B shows representative micrographs for MDA-MB-231 and MDA-MB-435 and the percentage of cells that demonstrated lamellipodia was quantified for each treatment from 10 representative microscopic fields according to the present invention.

FIG. 6A shows a representative Western blot for MDA-MB-435 cells treated with vehicle (0) or 2 or 4 μM EHop-016 for 24 h according to the present invention.

FIG. 6B shows quantification of positive bands from Western blots (65 kDa) using ImageJ software according to the present invention.

FIG. 6C shows representative micrographs of propidium iodide-stained cells for each treatment at ×200 magnification and the percentage of cells that migrated to the underside of a membrane with 8-μm diameter pores, relative to vehicle (100%) according to the present invention.

FIG. 8A shows an alternative docking conformations of EHop-016 into the putative GEF binding pocket of Rac1 with lowest energy conformation of cluster of size 13 and energy of −7.61 kcal/mol according to the present invention.

FIG. 8B shows an alternative docking conformations of EHop-016 into the putative GEF binding pocket of Rac1 with lowest energy conformation of cluster of size 21 and energy of −7.41 kcal/mol according to the present invention.

FIG. 9 shows the effect of EHop-016 on Rac/Tiam-1 binding domain (DH/PH) interaction according to the present invention.

Figure 2:
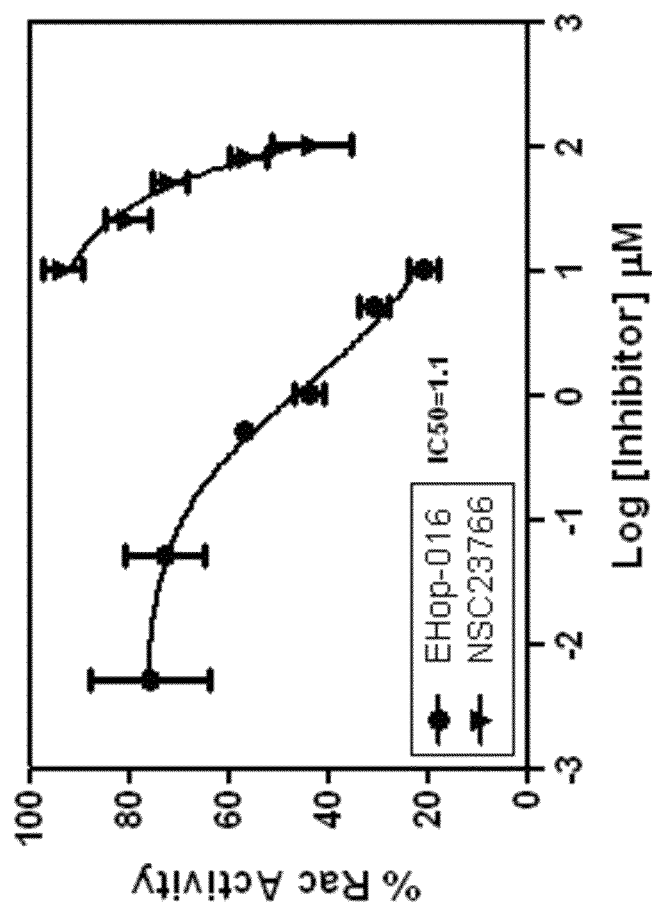
FIG. 2 shows a plot indicating the inhibitory effect of EHop-016 and NSC-23766 on Rac activity according to the present invention.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Experimental Procedures
Synthesis of EHop-016

$^1$H and $^{13}$C NMR spectra were recorded on a Bruker 400 MHz Spectrometer. Mass spectra were obtained on a Hewlett Packard 6890N GC/MS Spectrometer. All chemicals were purchased from Sigma Aldrich Chemical Company. The synthesis of EHop-016 (5) was performed in two steps according to the reaction scheme provided in FIG. 1(A), and carried out analogous to the procedure described in (58). (2-Chloro-pyrimidin-4-yl)-(9-ethyl-9H-carbazol-3-yl)-amine 3 was obtained as a pure compound in a yield of 53%. The product was identified with TLC, NMR and GC/MS. $R_f$=0.23 (3:1, Hexane-Ethyl Acetate); $^1$H NMR (DMSO-$d_6$, 400 MHz) δ 1.32 (t, J=6.9 Hz, 3H), 4.45 (q, J=6.6 Hz, 2H), 6.72 (s, 1H), 7.20 (t, J=7.36 Hz, 1H), 7.47 (t, J=7.30 Hz, 1H), 7.56 (s, 1H), 7.62 (t, J=8.68 Hz, 1H), 8.11 (t, J=7.36 Hz, 1H), 8.27 (s, 1H), 10.1 (s, 1H); $^{13}$C (DMSO-$d_6$, 100 MHz) δ 13.7, 37.0, 109.2, 109.4, 115.0, 118.7, 120.3, 121.3, 121.9, 122.3, 125.9, 129.9, 136.9, 140.0, 156.9, 159.6, 162.4; LRGC-MS m/z (rel %): [M]$^+$ 276 (100), [M-Cl]$^+$ 241 (40), [M-$C_5H_5N_3$Cl]$^+$ 134 (26). N$^4$-(9-Ethyl-9H-carbazol-3-yl)-N2-(3-morpholin-4-yl-propyl)-pyrimidine-2,4-diamine 5 (EHop-016) was obtained as a pure compound in a yield of 93%. The product was identified to be essentially pure by TLC and NMR: $R_f$=0.34 (9:1, $CH_2Cl_2$-MeOH); $^1$H NMR (DMSO-$d_6$, 400 MHz) δ 1.31 (t, J=7.0 Hz, 3H), 1.73 (m, 2H), 2.32 (m, 2H), 2.34 (t, J=6.89 Hz, 8H), 3.52 (m, 2H), 4.42 (q, J=7.0 Hz, 2H), 5.98 (d, J=5.7 Hz, 1H), 6.69 (t, J=5.3 Hz, 1H), 7.16 (t, J=7.4, 1H), 7.43 (t, J=7.2 Hz, 1H), 7.53 (t, J=9.0 Hz, 4H), 7.81 (d, J=5.4 Hz, 1H), 8.10 (s, 1H), 8.66 (s, 1H), 9.1 (s, 1H); $^{13}$C (DMSO-$d_6$, 100 MHz) δ 13.7, 26.2, 36.9, 53.4, 56.3, 66.2, 108.9, 109.0, 118.2, 119.7, 120.2, 122.0, 122.2, 125.6, 132.5, 135.5, 139.9, 159.8, 160.9, 162.1.

Docking of Ehop-16 into the Crystal Structure of Rac1

For molecular docking, Autodock 4.0 with AutodockTools 1.5.4 as the graphical user interface was used. The coordinates of the crystal structure from the Rac1-NSC23766 complex were obtained. EHop-016 was drawn using ChemDraw Ultra 7.0 and energy minimized with MOPAC AM1 in Chem3D Ultra 7.0. After removing NSC23766 from the crystal structure, AutodockTools was used to prepare the receptor and EHop-016 for docking, and to create a grid of 60 Å×60 Å×60 Å with a grid spacing of 0.375 Å centered on the original position of NSC23766. A flexible docking of 100 GA-runs was performed with the number of individuals in population set to 200 and the maximum number of energy evaluations set to 25,000,000, with other parameters accepted as suggested by AutodockTools, which also was used for clustering (RMS=2 Å) of the results obtained.

Rac Activity Assays

Rac activity was determined from lysates of the MDA-MB-435 human metastatic cancer cell line (from ATCCC) that our group has previously shown to have high endogenous Rac activity. MDA-MB-435 cells in culture media were treated with vehicle (0.1% DMSO), or varying concentrations of Ehop-16 (0-10 µM) for 24 h. Rac1 activity was determined as previously described by our group, using the G-LISA Rac1 Activation Assay kit (Cytoskeleton, Inc., Denver, Colo.).

For generation of $IC_{50}$ curves for each inhibitor (EHop-016 or NSC-23766) data from three independent duplicate experiments was pooled and four parameter dose-response curves were fitted using the non-linear regression function of Graph-Pad Prism®.

Rho GTPase Activity Assays

Rho, Rac, and Cdc42 activities were analyzed from MDA-MB-435 cell lysates by pulldown assays using GST-Rho binding domain from Rhotekin to isolate active GTP bound Rho, and a GST-p21 binding domain of PAK1 to isolate active Rac.GTP or Cdc42.GTP. Active and total Rho GTPases were identified by western blotting with specific antibodies: anti RhoA, anti Rac (1,2,3), anti Rac3, or anti Cdc42 (Cell Signaling Technology, Inc., Danvers, Mass.).

Cell Viability Assays

MDA-MB-435 or MCF-10 mammary epithelial cells (from ATCC) were incubated in vehicle (0.1% DMSO) or varying concentrations of EHop-16 (0-10 µM) for 24 hrs. Cell viability was measured using the MTT [3-(4,5-dimethylthiazol-2-yl)-2,5-diphenyl tetrazolium bromide] cell survival and proliferation kit (Millipore, Inc., Billerica, Mass.) according to manufacturer's instructions.

Western Blotting

Cell lysates or pulldowns were western blotted using routine laboratory procedures. Anti-RhoA, -Rac (1,2,3), -Cdc42,-p-PAK$^{Thr423}$ antibodies were from Cell Signaling Technology, Inc., Danvers, Mass. Anti Vav2 was from Zymed, San Francisco, Calif.; and Rac3, PAK1, Tiam-1, and Trio antibodies were from Santa Cruz Biotechnology, Inc., Santa Cruz, Calif.

Precipitation of Activated GEFs with Recombinant Mutant Rac1 (G15A) Protein

MDA-MB-435 cells in culture media were lysed in 1% Triton X-100, 20 mM HEPES, pH 7.4, 150 mM NaCl, 5 mM $MgCl_2$, and protease inhibitors and processed. Equal amounts of protein from clarified lysates were incubated for 1 h at 4° C. with glutathione agarose beads conjugated to GST-Rac1 (G15A) nucleotide free mutant (Cell Biolabs, San Diego, Calif.), that were pre-incubated (for 1 h) with vehicle or 2 or 4 mM EHop-016. The beads were washed and the lysates and pulldowns immunoblotted for Tiam-1, Trio, or Vav2.

Interaction of Tiam-1DH/PH Domain with Rac1(G15A)

His-tagged Tiam-1 DH-PH pET construct was transformed into Rosetta DE3 E. Coli cells and clarified lysates purified by batch affinity chromatography using His-Select Nickel Affinity Gel (Sigma). Tiam-1 was eluted with 300 mM Imidazole and separated by a FPLC size exclusion Superdex 200 column. Purity of Tiam-1 fraction at 1.7 mg/ml was observed to be >95% by SDS-PAGE. GST-Rac1(G15A) glutathione agarose or glutathione agarose beads alone were pre-incubated with varying concentrations of EHop-016 or NSC-23766 for 1 h in lysis buffer (1% Igepal, 20 mM HEPES, 150 mM NaCl, 5 mM $MgCl_2$, pH 7.5). Purified His-Tiam-1 DH/PH domain was added at a concentration of 2:1 Rac1(G15A): Tiam-1, and incubated for another hr at 4° C. Pulldowns were washed 3× in 1% Igepal buffer and 1× in HEPES buffer and western blotted with an anti-His antibody to visualize His-Tiam-1DH/PH domain protein.

Fluorescence Microscopy

Metastatic human cancer cell lines MDA-MB-435 and MDA-MB-231 (in DMEM with 10% FBS) were treated with vehicle (0.1% DMSO) or EHop-016 at 2 and 4 µM for 24 hrs. Cells were fixed, permeabilized, and stained with Rhodamine phalloidin to visualize F-actin.

Cell Migration Assays

Quiescent MDA-MB-435 cells were treated with vehicle or varying concentrations of EHop-016 (0-5 µM) for 24 hrs. Exactly 2×10$^5$ cells were placed on the top well of Transwell chambers (Corning Life Sciences, Lowell, Mass.) with media containing 10% FBS in the bottom well. The number of cells that migrated to the underside of the membrane following 4 h incubation was quantified for each treatment.

Results

Synthesis of EHop-016

The inhibition of Rac1 activity has been proposed as a strategy for the prevention of cancer metastasis. However, the frequently utilized small molecule Rac1 inhibitor NSC23766 only has a moderate biological effect on the highly metastatic cancer cell line MDA-MB-435, even at high concentrations; thus, illustrating the need for more potent and effective inhibitors. Our group recently reported the synthesis of novel NSC23766 derivatives that showed increased Rac1 inhibitory activity in MDA-MB-435 cells with a considerable reduction of cell functions regulated by Rac. Further research lead to the identification of EHop-016, which was synthesized according to the procedure described in FIG. 1(A).

Briefly, 2,4-dichloropyrimidine (1) was reacted with 3-amino-9-ethylcarbazole (2) by heating in iso-propanol in the presence of N,N-diisopropylethylamine. Separation of the regioisomers provided the pure 4-substituted pyrimidine derivative (3), which was reacted with 4-(3-Aminopropyl) morpholine (4) in sec-butanol under microwave heating in the presence of N,N-diisopropylethylamine to provide EHop-016 (5).

Molecular Docking of EHop-016

NSC23766 was designed to prevent the activation of Rac1 by binding to the region where several GEFs interact with Rac1, thus inhibiting its activation. This mode of action was recently confirmed via analysis of the crystal structure of Rac1 with NSC23766. For the design of novel, more potent inhibitors, we desired to improve the activity and maintain the selectivity profile of NSC23766. Therefore, in order to obtain a similar binding interaction for the new inhibitors, the core structural features of NSC23766 were maintained, including a central pyrimidine core, an aromatic 4-substituent and an amino group containing 2-substituent, both connected to the pyrimidine core via nitrogen atoms. Molecular docking, to study the binding interactions of EHop-016 with Rac1, demonstrated that EHop-016 can bind to Rac1 in different orientations into the cleft formed by amino acids Pro34, Thr35, Val36, Phe37, Asp38, Asn39, Trp56, Asp57, Thr58, Ala59, Tyr64, Leu67, Arg68, Leu70 and Ser71. Clustering of the docking results revealed that the largest cluster (size=29) also had the docking conformation with the lowest energy (−7.91 kcal/mol), and the most favorable conformation is illustrated in FIG. 1B, together with the position of NSC23766 in the crystal structure of the Rac1-NSC23766 complex. Whereas NSC23766 is stretched over the surface of Rac1, similar to other novel Rac1 inhibitors that were recently identified (60), EHop-016 appears to favor a bent conformation that binds to a deeper binding pocket similar to the N,N-diethylamino group of NSC23766. In its energetically most favorable conformation, the binding of EHop-016 is strengthened by two hydrogen bonding interactions with residues Asp38 and Asn39. Furthermore, EHop-016 has a close interaction with Trp56, which has been shown to be critical for binding of Rac to its GEFs. Two smaller clusters (sizes=13 and 21), with lowest energy conformations of −7.61 and −7.41 kcal/mol respectively, dock into the same cleft albeit in a somewhat different mode as shown in FIGS. 8A-8B. Based on the above molecular docking results, structural similarity to NSC23766, and the biological activity profile described herein, it is reasonable to postulate that EHop-016 also interferes with binding of Rac1 with its GEFs via binding to the three-way junction site that contains the switch I, switch II, and β loops of the effector region of Rac that interacts with the dbl homology (DH) domain of Rac-GEFs. The crystal structures of a complex of the binding domains of the homologous GEF Vav1 with Rac1 were previously described. Using this information, analysis of binding interactions indicates that unlike NSC23766, EHop-016 interacts with several of the amino acid residues that form the putative binding pocket of Vav1 with Rac1. More specifically, of the residues that are calculated to interact with EHop-016, Vav1 interacts with residues Thr35, Val36 and Asn39 of switch I, and residues Ala59 and Tyr64 of switch II as shown in FIG. 1(B). Therefore, it is suggested that EHop-016 binds tightly to key amino acid residues of Rac1, potentially inhibiting interaction with Vav.

EHop-016 is a Potent Inhibitor of Rac1

The potential of EHop-016 to inhibit Rac activity was determined in the highly metastatic human cancer cell line MDA-MB-435 that was previously reported by our group to contain high endogenous Rac activity. MDA-MB-435 cells were treated for 24 h with varying concentrations of EHop-016, and for comparison, NSC23766. Rac activity from cell lysates was measured using the G-LISA Rac1 activation assay. The concentration curves in FIG. 2 demonstrate that EHop-016 inhibits Rac1 activity in MDA-MB-435 cells with an $IC_{50}$ of 1.1 µM, while the $IC_{50}$ for NSC23766 in the same cell line was 95 µM. Thus, EHop-016 is approximately 100 times more potent than NSC23766 and 10-50 times more potent than other currently available Rac inhibitors.

Effect of EHop-016 on the Activity of Other Rho Family GTPases

Figure 3A:
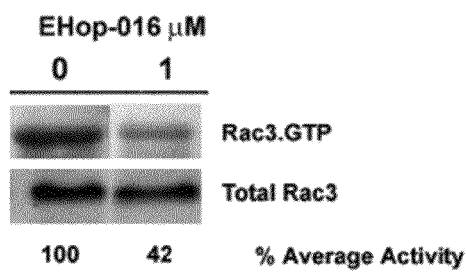
FIG. 3A shows a representative Western blot of pull-downs immunostained for Rac3-GTP (top row) or total Rac3 in cell lysate (bottom row) (n=3) according to the present invention.
Figure 3B:
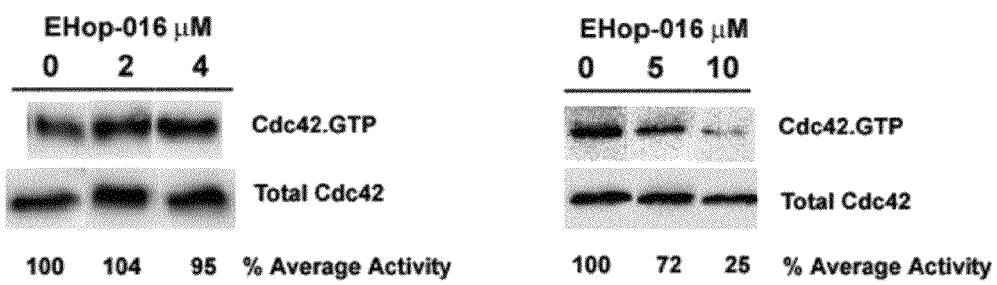
FIG. 3B shows representative Western blots of pull-downs immunostained for Cdc42-GTP (top row) or total Cdc42 in cell lysate (bottom row) (n=2) according to the present invention.
Figure 3C:
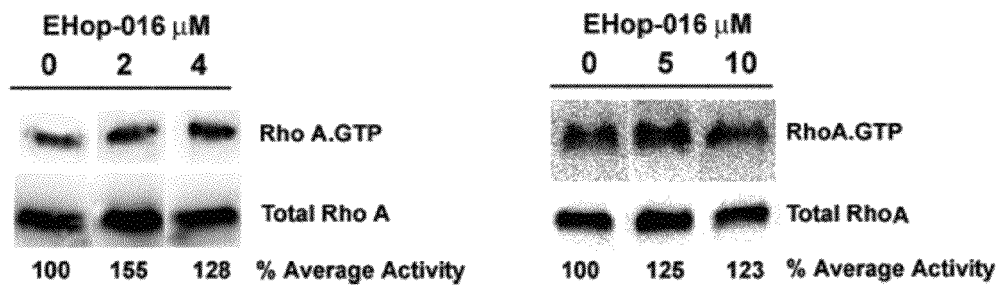
FIG. 3C shows representative Western blots of pull-downs immunostained for RhoA-GTP (top row) or total RhoA in cell lysate (bottom row) (n=3) according to the present invention.

In order to investigate the selectivity of EHop-016, we studied its effect on other Rho family GTPases. Similar to Rac1, the Rac isoform Rac3 that is also overexpressed in cancer cells was inhibited by 58% at a concentration of 1 µM EHop-016 as shown in FIG. 3(A). This is expected since Rac1 and Rac3 demonstrate significant structure similarity and are activated by the same GEFs. EHop-016 did not affect the activity of the Rac homolog Cdc42 at 2 or 4 µM but inhibited Cdc42 activity by 28% at 5 µM and 74% at 10 µM (FIG. 3B). Therefore, EHop-016 may not bind the similar DH-interacting domain of Cdc42 as tightly as Rac but is able to inhibit Cdc42 activity at higher concentrations. In contrast, the activity of the closely related Rho GTPase RhoA was increased by ~1.3-fold in response to 2, 4, 5, or 10 µM EHop-016. Increased Rho activity, when Rac is being inhibited by EHop-016, may be a compensatory mechanism. This is expected to increase Rho-regulated assembly of F-actin into stress fibers and further inhibit Rac-mediated lamellipodia formation and directed migration (1;4;10).

EHop-016 Inhibits the Association of Active Vav2 with a Rac1 (G15A) Mutant Fusion Protein To investigate a mechanism for the inhibition of Rac by EHop-016, the active Rac-GEFs in MDA-MB-435 cells were detected from pulldowns of a glutathione agarose conjugated GST fusion protein of a Rac1 nucleotide-free mutant Rac1 (G15A) that has a high affinity for activated GEFs (66;69). As shown in FIG. 4(A), in the highly metastatic MDA-MB-435 cell line with elevated Rac activity, Vav2 appears to be more abundant compared to Tiam-1 and Trio. Even though equal amounts of total protein were used for western blotting, it is possible that the differences in GEF expression may reflect the relative affinities to their specific antibodies. Moreover, in MDA-MB-435 cells growing in 10% serum, only active Vav2 was pulled down with the GST-Rac1 (G15A) and not Tiam-1 or Trio as shown in FIG. 4A). We show that the association of Vav2 with Rac1(G15A) was inhibited by 4 µM EHop-016 to ~50% compared to controls in a statistically significant manner (p<0.005) as shown in FIGS. 4(B) and 4(C). Since, we did not detect association of Tiam-1 with Rac1(G15A) under our experimental conditions, the effect of EHop-016 on the interaction of Rac1 and Tiam-1 could not be measured in vivo.

When Rac1(G15A) beads were incubated with a purified Tiam-1 DH/PH domain, the active Tiam-1 was associated with the Rac1(G15A) beads. However, EHop-016 inhibited the interaction of Tiam-1 DH/PH domain with Rac1(G15A) only at concentrations 40 µM. At 5 µM, EHop-016 did not affect the interaction of Tiam-1 DH/PH domain with Rac1 (G15A) beads. At 50 µM EHop-016, there was a statistically significant 64% inhibition of Tiam-1/Rac1(G15A) interaction. In contrast, the parent compound NSC23766 inhibited the Rac1(G15A) interaction with purified Tiam-1 DH/PH domain at both 5 and 50 µM as shown in FIGS. 4(D) and 4(E). Therefore, the concentrations at which EHop-016 inhibited Tiam-1/Rac1 interaction was 10 times higher than the physiological concentrations (2-4 µM) at which EHop-016 inhibited Rac activity or the interaction of Rac1 (G15A) with Vav2 in MDA-MB-435 cell lysates.

EHop-016 Reduces Rac-Regulated Cell Functions

Rac is a central regulator of lamellipodia and invadopodia that control directed mesenchymal migration and invasion of cancer cells. Therefore, we investigated the effect of EHop-016 on Rac activity and lamellipodia formation in the low metastatic breast cancer cell line MDA-MB-231 and the high metastatic MDA-MB-435 cells. As shown in FIG. 5(A), for equal amounts of total protein, Rac expression and activity in MDA-MB-231 cells were less when compared to MDA-MB-435 cells. EHop-016 at 2 µM (double the $IC_{50}$ for Rac inhibition) inhibited the Rac activity of MDA-MB-435 cells by 79% and by 93% at 4 µM. The Rac activity of MDA-MB-231 cells was also inhibited by EHop-016 with an $IC_{50}$ of ~3 µM as shown in FIG. 5(A). Therefore, EHop-016 is more efficient at inhibiting MDA-MB-435 cells with elevated Rac activity. Lamellipodia extension was determined in cells stained with Rhodamine phalloidin to localize F-actin. Treatment for 24 h with EHop-016 at 2 and 4 µM inhibited lamellipodia formation in both MDA-MB-231 and MDA-MB-435 cells. Results show that close to 100% of control cells demonstrated lamellipodia and membrane ruffles. Following EHop-016 treatment, at 4 µM in MDA-MB-231 cells and both 2 and 4 µM in MDA-MB-MB-435 cells, only ~30% of the cells extended lamellipodia. Therefore, EHop-016 at concentrations that inhibit Rac activity significantly inhibited lamellipodia extension to a similar extent, indicating a direct regulatory effect of Rac activity on lamellipodia extension as shown in FIG. 5(B). However, EHop-016 did not affect the extension of filopodia that are regulated by Cdc42. These data indicate a specific role for EHop-016 in inhibiting Rac-directed actin structures.

The effect of EHop-016 on Rac action was also determined by analyzing the activity of the Rac downstream effector PAK that regulates Rac-mediated lamellipodia extension and directed cell migration. By western blotting with a specific antibody to the kinase active form of PAK1 with a phospho-Thr 423, we show that EHop-016 dramatically inhibits PAK activity at both 2 and 4 µM as shown in FIG. 6(A). Since Rac/PAK signaling regulates directed cell migration, the effect of EHop-016 at 0-5 µM was determined on migration of MDA-MB-435 cells by using a Transwell assay. As shown in FIG. 6(B), treatment with 2 and 5 µM EHop-016 reduced directed cell migration by ~60% at concentrations that reduced Rac activity by ~80% as shown in FIG. 2 and FIGS. 4A-4E. It is possible that Rac may not be the only regulator of cell migration in this highly invasive cancer cell line. Since equal cell numbers were placed on the top wells of the Transwell chambers and the migration assays were conducted for only four hours, we do not expect effects of reduced cell viability or cell death to affect data interpretation.

These experiments were conducted in culture media containing 10% FBS to recapitulate the endogenous cellular environment. Since serum contains activators of Rac, Rho, and Cdc42, this experimental design does not allow for the analysis of Rac regulation in the absence of other cytoskeletal regulators.

Effect of EHop-016 on Cell Viability

Figure 7:
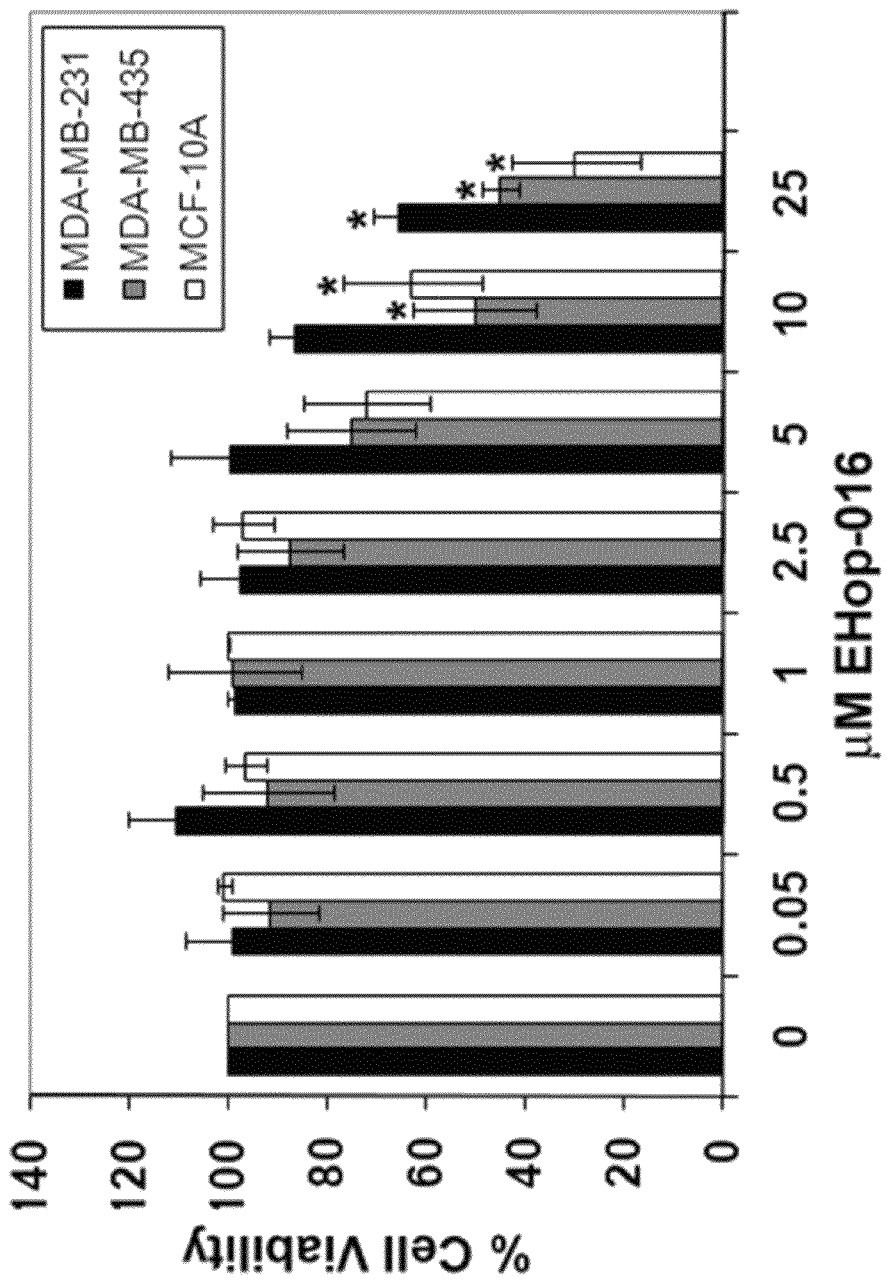
FIG. 7 shows the effect of EHop-016 on cell viability of metastatic breast cancer cells and mammary epithelial cells according to the present invention.

We tested the viability of MDA-MB-231 and MDA-MB-435 cancer cells, and MCF10A transformed mammary epithelial cells in the presence of EHop-016. EHop-016 at the $IC_{50}$ of 1 or 2 µM did not significantly affect mammary epithelial or cancer cell viability as shown in FIG. 7. At 5 µM, EHop-016 decreased MDA-MB-435 and MCF-10A cell number by ~30% compared to controls; however, this was only a trend. In these cell lines, cell viability was significantly decreased to ~50% at 10 µM, while all three cell lines demonstrated a significant reduction in cell viability at 25 µM. Therefore, further inhibition of Rac and Cdc42 activity by EHop-016 at concentrations above 5 µM may lead to additional inhibition of Rac and Cdc42-mediated effects on cell cycle progression and growth.

Discussion

Herein, we describe the synthesis and characterization of a potent and specific small molecule inhibitor of Rac, a key signaling protein that regulates cancer progression and metastasis. Recent studies have demonstrated that inhibition of Rac activity, and thus cancer cell invasion, is a viable strategy for the treatment of breast cancer metastasis. Current small molecule inhibitors of Rac activity such as NSC23766 and EHT 1864 are effective at high concentrations, approximately 50-100 µM for NSC23766 and 10 µM for EHT 1864, and the inhibitory efficiency appears to be dependent on cell type. As we have previously shown, high metastatic variants of MDA-MB-435 demonstrate high endogenous Rac activity, without changes in Rac expression. Therefore high Rac-GEF activity may explain the moderate biological activity of NSC23766 in metastatic cancer cells.

Our objective was to utilize the structure of NSC23766 as a lead for the development of a more potent inhibitor that similar to NSC23766, binds specifically into a surface groove of Rac1 known to be critical for GEF interaction. Docking studies demonstrated that EHop-016 binds to the effector domain of Rac1 with a deeper interaction in the switch 1 and switch II regions than NSC23766. Therefore, EHop-016 has the potential to block Rac-GEFs distinct from the action of NSC23766. Moreover, EHop-016 was found to be a ~100-fold more potent inhibitor of Rac activity than NSC23766 in the metastatic MDA-MB-435 cancer cell line. EHop-016 is also a 10-50-fold more effective inhibitor of Rac1 than recently reported NSC23766 derivatives. Our data demonstrate that EHop-016 is specific for Rac isoforms Rac1 and Rac3. Cdc42, a close homolog that is not activated by the Rac-GEFs Tiam-1, Trio, or P-Rex, but is activated by Vav2 is inhibited by EHop-016 at higher concentrations. Therefore, EHop-016 may be specific for Rac at lower physiologically relevant concentrations when Rac1 is the preferred partner of Vav2. Because of its structural similarity to NSC23766, as well as its biological activity profile and molecular docking findings, it is proposed that EHop-016 also interacts with the effector region of Rac, where it inhibits the binding of GEFs. In fact, we found that EHop-016 at 50 mM, a concentration much higher than its physiologically effective 2 mM concentration, may impede the interaction of active Tiam-1 with Rac1(G15A) in vitro. However, the Tiam-1 specific inhibitor NSC23766 blocked the interaction of Tiam-1 and Rac1 (G15A) to a similar extent at a lower (5 mM) concentration compared to EHop-016; thus, indicating that EHop-016 is not specific to Tiam-1. Similarly, EHop-016 is probably not specific to Trio, a GEF that shares the amino acid residue Trp 56 in Rac1 with Tiam-1, as a critical determinant for their activity.

The significant finding that EHop-016 inhibits the interaction of Vav2 with Rac1 at physiologically relevant concentrations is central to the further development of this compound as an inhibitor of cancer malignancy. Both Vav2 and Tiam1 have been implicated in Rac-mediated transformation and invasion/metastasis. To our knowledge, no specific inhibitors for Vav2/Rac interaction have been described. Using an established method for detecting active Rac-GEFs from cell lysates, we found that Vav2, and not Tiam-1 or Trio, was active in the MDA-MB-435 cell line in culture. It is possible that low active levels of Tiam-1 and Trio were not detected due to the limited sensitivity of immunoblotting. Another alternative is that the serum in culture media activated Vav2 preferentially and future studies will be conducted in quiescent cells following epidermal growth factor receptor (EGFR)/human epidermal growth factor receptor 2 (HER2) stimulation, which is expected to activate both Vav2 and Tiam-1.

Vav2 has been shown to act as an exchange factor for Rac, Rho, and Cdc42 in vitro. The increased Rho activity following EHop-016 treatment may be due to a complex biological response to Rac inhibition. Studies have shown that Rac activation can inhibit Rho activity and vice versa. Indeed, disparate roles have been proposed for Vav2 activated Rho and Rac in mammary epithelial cells; thus, suggesting that EHop-016 mediated inhibition of Rac/Vav2 interaction may result in enhanced Vav2 availability for Rho activation.

Figure 10:
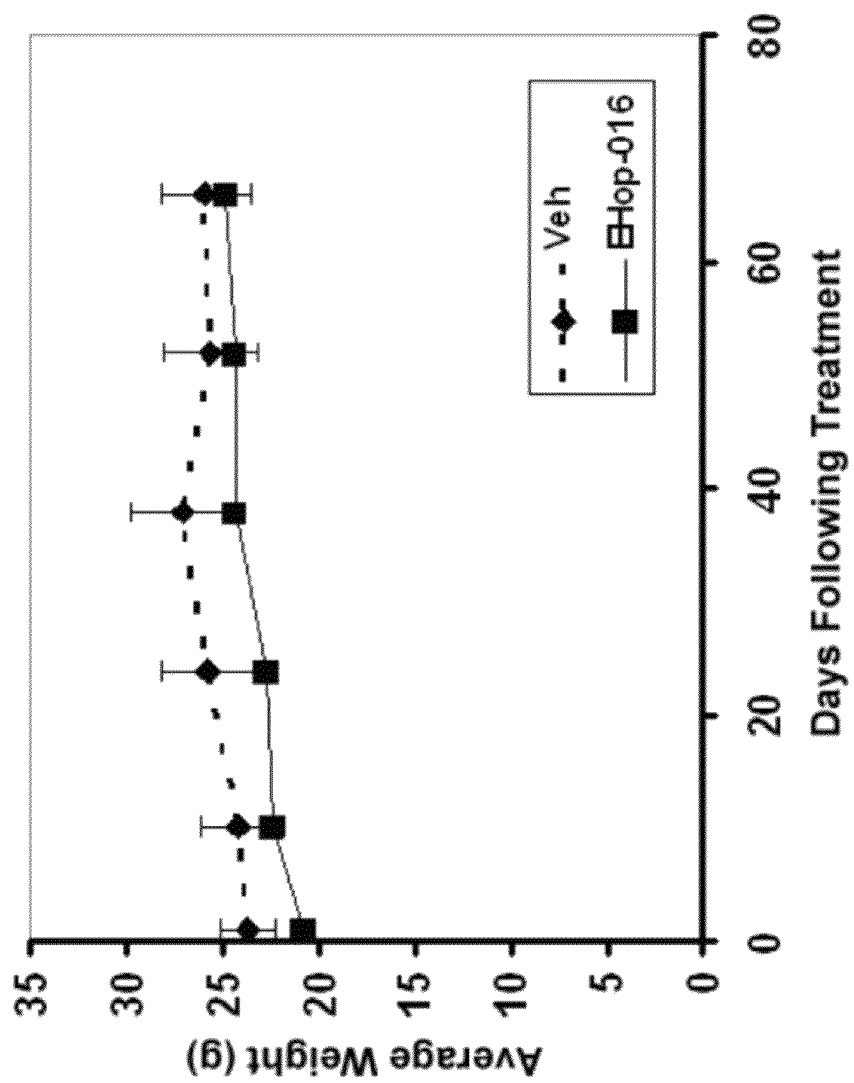
FIG. 10 shows the weight change of mice following vehicle or EHop-016 administration according to the present invention.

Herein, we show that cell viability is not affected by EHop-016 at the low concentrations that specifically inhibit Rac and PAK activities and actin cytoskeletal changes. Racs and Cdc42 have been shown to affect cell survival via a number of signaling pathways including phosphoinositide 3-kinase (PI3-K), nuclear factor kB (Nf-κB), and Jun kinase (JNK)/p38 mitogen activated protein kinases (MAPK). Accordingly, cell viability is affected at higher concentrations (5 mM), when EHop-016 inhibits both Rac and Cdc42 activities. In preliminary studies, we have tested the effect of oral and intraperitoneal administration of EHop-016 to athymic nude mice at 1 mg/kg body weight once a week for 9 weeks and found no change in body weight or gross indications of toxicity as shown in FIG. 10.

Results show that EHop-016 reduced lamellipodia and directed cell migration by 60-70% at concentrations that do not affect cell viability but inhibit Rac activity by ~80%. At a concentration of 2 µM, EHop-016 exerted a dramatic reduction in lamellipodia formation without affecting Cdc42-induced filopodia extension. The concentration at which EHop-016 inhibited lamellipodia extension and cell migration is approximately 10-50 fold less than the reported concentrations of NSC23766 and EHT1864 required to inhibit lamellipodia extension and cell migration. This result is similar to our previous report of decreased MDA-MB-435 cell migration in the presence of other NSC23766 derivatives that inhibit Rac activity. Even though a single report demonstrated increased migration of MDA-MB-435 and MDA-MB-231 metastatic breast cancer cells following 50-100 µM NSC23766, in our hands, treatment with 100 µM NSC23766 for 24 h resulted in a 75% decrease in MDA-MB-435 cell migration (data not shown). Moreover, there are several reports of decreased cell migration in metastatic breast cancer cells following direct inhibition of Rac1 and Rac3 by expression of dominant negative Rac and siRNA knockdown of Rac expression, or by indirect inhibition of Rac by blocking upstream effector activity.

In conclusion, we have shown that EHop-016 is an effective Rac-specific inhibitor at low micromolar concentrations. EHop-016 substantially inhibits Vav2 interaction with Rac, Rac-activated PAK1, lamellipodia formation, and cell migration. At concentrations above 5 µM, EHop-016 also inhibits Cdc42 activity and cell viability. Since Rac/PAK activity is central to cancer cell migration and invasion, EHop-016 appears to be a promising candidate for further development as a pharmacological inhibitor of Rac activity in metastatic cancer cells. In addition, EHop-016 could prove to be a valuable, more potent probe for the study of Rac-regulated cellular processes.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A compound $N^4$-(9-ethyl-9H-carbazol-3-yl)-N2-(3-morpholin-4-yl-propyl)-pyrimidine-2,4-diamine of the chemical structure:

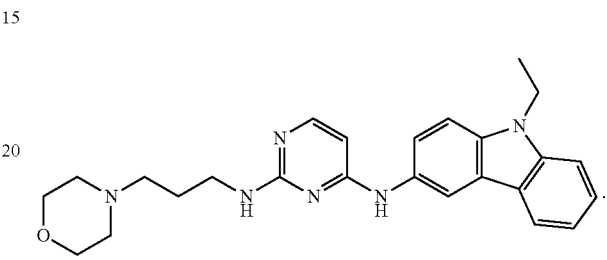

2. A method of synthesizing the compound of claim 1 comprising reacting 2,4-dichloropyrimidine with 3-amino-9-ethylcarbazole to obtain (2-chloro-pyrimidin-4-yl)-(9-ethyl-9H-carbazol-3-yl)-amine and reacting the (2-chloro-pyrimidin-4-yl)-(9-ethyl-9H-carbazol-3-yl)-amine with 4-(3-aminopropyl)morpholine.

* * * * *